US010618855B2

(12) United States Patent
Pan et al.

(10) Patent No.: US 10,618,855 B2
(45) Date of Patent: Apr. 14, 2020

(54) CATALYST AND METHOD FOR SYNTHESIS OF AROMATIC HYDROCARBONS THROUGH DIRECT CONVERSION OF SYNTHESIS GAS

(71) Applicant: DALIAN INSTITUTE OF CHEMICAL PHYSICS, CHINESE ACADEMY OF SCIENCES, Dalian (CN)

(72) Inventors: Xiulian Pan, Dalian (CN); Junhao Yang, Dalian (CN); Feng Jiao, Dalian (CN); Yifeng Zhu, Dalian (CN); Xinhe Bao, Dalian (CN)

(73) Assignee: DALIAN INSTITUTE OF CHEMICAL PHYSICS, CHINESE ACADEMY OF SCIENCES, Dalian (CN)

( * ) Notice: Subject to any disclaimer, the term of this patent is extended or adjusted under 35 U.S.C. 154(b) by 0 days.

(21) Appl. No.: 16/081,748

(22) PCT Filed: Jul. 12, 2016

(86) PCT No.: PCT/CN2016/089725
§ 371 (c)(1),
(2) Date: Aug. 31, 2018

(87) PCT Pub. No.: WO2017/210954
PCT Pub. Date: Dec. 14, 2017

(65) Prior Publication Data
US 2019/0031575 A1  Jan. 31, 2019

(30) Foreign Application Priority Data

Jun. 7, 2016  (CN) .......................... 2016 1 0397763

(51) Int. Cl.
*B01J 29/06* (2006.01)
*C07C 1/04* (2006.01)
*B01J 29/40* (2006.01)
*B01J 23/889* (2006.01)
*B01J 21/00* (2006.01)
*B01J 23/00* (2006.01)
*B01J 35/02* (2006.01)
*B01J 37/00* (2006.01)
*B01J 35/10* (2006.01)
(Continued)

(52) U.S. Cl.
CPC ............. *C07C 1/043* (2013.01); *B01J 21/005* (2013.01); *B01J 21/06* (2013.01); *B01J 21/066* (2013.01); *B01J 23/005* (2013.01); *B01J 23/06* (2013.01); *B01J 23/26* (2013.01); *B01J 23/34* (2013.01); *B01J 23/8892* (2013.01); *B01J 29/40* (2013.01); *B01J 29/405* (2013.01); *B01J 29/44* (2013.01); *B01J 29/48* (2013.01); *B01J 35/0006* (2013.01); *B01J 35/0013* (2013.01); *B01J 35/023* (2013.01); *B01J 35/026* (2013.01); *B01J 35/1057* (2013.01); *B01J 35/1061* (2013.01); *B01J 35/1066* (2013.01); *B01J 35/1095* (2013.01); *B01J 37/0036* (2013.01); *B01J 21/04* (2013.01); *B01J 2229/20* (2013.01); *C07C 2523/06* (2013.01); *C07C 2523/26* (2013.01); *C07C 2523/34* (2013.01); *C07C 2529/40* (2013.01); *C07C 2529/44* (2013.01); *C07C 2529/48* (2013.01)

(58) Field of Classification Search
CPC ... B01J 29/40; B01J 29/48; B01J 29/44; B01J 29/405; B01J 35/023; B01J 35/026; B01J 35/1061; B01J 35/1066; B01J 35/0013; B01J 35/0006; B01J 35/1057; B01J 35/1095; B01J 21/04; B01J 21/06; B01J 21/005; B01J 21/066; B01J 2229/20; B01J 37/0036; C07C 2529/40; C07C 2529/44; C07C 2529/48; C07C 1/043; C07C 1/041; C07C 1/0425; C07C 1/0455; C07C 15/04; C07C 15/06; C07C 15/08
USPC ........ 502/60, 63, 64, 67, 69, 73, 77; 585/469
See application file for complete search history.

(56) References Cited

U.S. PATENT DOCUMENTS 5,865,988 A    2/1999  Collins et al.
2016/0024393 A1*  1/2016  Beech, Jr. ................ B01J 23/70
                                                      585/321

FOREIGN PATENT DOCUMENTS

CN    105566047 A    5/2016
EP    0051326 B1    7/1984
RU    2089533 C1    9/1997

OTHER PUBLICATIONS

Desheng Wang et at, "Direct Conversion of Syngas into Aromatics over Bifunctional Fe/Mno—ZnZSM-5 Catalyst", Chinese Journal of Catalysis, 2002, 23, vol. 4, 333-335 (English abstract included).
(Continued)

*Primary Examiner* — Elizabeth D Wood
(74) *Attorney, Agent, or Firm* — Enshan Hong; VLP Law Group LLP

(57) ABSTRACT

Synthesis of aromatic hydrocarbons from synthesis gas in a fixed bed or a moving bed reactor loaded with a composite catalyst comprising Catalyst Component A and Catalyst Component B mixed via a mechanical mixing mode, wherein the active ingredient of the Catalyst Component A is active metal oxides; and the Catalyst Component B is one or both of ZSM-5 zeolite and metal modified ZSM-5; the pressure of the synthesis gas is 0.1-6 MPa; the reaction temperature is 300-600° C.; and the space velocity is 500-8000 $h^{-1}$. The reaction process has a high product yield and selectivity, with the selectivity of aromatics reaching 50-85%, while the selectivity of the methane byproduct is less than 15%.

12 Claims, No Drawings

(51) Int. Cl.
*B01J 21/06* (2006.01)
*B01J 23/06* (2006.01)
*B01J 23/26* (2006.01)
*B01J 23/34* (2006.01)
*B01J 29/44* (2006.01)
*B01J 29/48* (2006.01)
*B01J 35/00* (2006.01)
B01J 21/04 (2006.01)

(56) References Cited

OTHER PUBLICATIONS

Qiangu Yan, "Synthesis of Aromatic-Rich Gasoline-Range Hydrocarbons from Biomass-Derived Syngas over a Pd-Promoted Fe/Hzsm-5 Catalyst", Energy Fuels, 2014, 28, 2027-2034.
Kaoru Fujimoto et al., "Synthesis Gas Conversion Utilizing Mixed Catalyst Composed of CO Reducing Catalyst and Solid Acid", Journal of Catalysis, 1984, 87, 136-143.

* cited by examiner

CATALYST AND METHOD FOR SYNTHESIS OF AROMATIC HYDROCARBONS THROUGH DIRECT CONVERSION OF SYNTHESIS GAS

RELATED APPLICATIONS

This is a U.S. national stage of international application No. PCT/CN2016/089725 filed on Jul. 12, 2016, which claims priority from China Patent Application No. 20160397763.3 filed on Jun. 7, 2016, the entire content of which is incorporated herein as reference.

TECHNICAL FIELD

The present invention involves a technology for synthesis of aromatic hydrocarbons from synthesis gas, and particularly relates to a catalyst and a method for synthesis of aromatic hydrocarbons through direct conversion of synthesis gas.

BACKGROUND OF THIS INVENTION

Aromatic hydrocarbons, which refer to the hydrocarbons containing benzene ring structure, are one of basic products and basic raw materials, mainly including benzene, toluene, xylenes, ethylbenzene and the like, and are widely used in the production of chemical fibers, plastics, rubber and other chemical products. In recent years, with the worldwide continuous expansion of polyester production, the demand for PTA (terephthalic acid) and PX (p-xylene) has increased rapidly.

Traditionally, aromatics can be produced from petroleum. There are two technological routes for production of aromatics from petroleum. The first one involves naphtha catalytic reforming and aromatics are subsequently obtained by extraction from complex mixtures. The second one: the pyrolysis gasoline is hydrogenated and aromatic hydrocarbons with low value are extracted, which are then converted into high value added aromatic productions. The technology for producing aromatics from the petroleum routes are mature, but restricted by thermodynamic equilibrium, the PX content in the aromatic productions is low. Thus, further processing and enriching are needed through adsorption separation or crystallization separation, in order to reduce the loss of raw materials and energy consumption, and hence reducing the production cost of PX through the petroleum routes. Another source of the raw materials for production of the aromatic hydrocarbons is coal. The aromatics can be produced through coal chemical technologies (including coal gasification, coal coking, coal liquefaction, etc.) combined with petrochemical technologies, such as a technology for producing PX through toluene and methanol methylation. With the development of the oil refining industry, the proportion of aromatic hydrocarbons using petroleum as raw material is gradually increased, accounting for more than 98% outside of China and accounting for more than 85% in China. In recent years, the production capacity of aromatic hydrocarbons in China has increased significantly and reached a certain scale, but it still cannot meet the actual market demand. The aromatics and the ethylene are the two most important products in petro and chemical industries in China, which can be used to fabricate a range of other important chemicals and polymers, such as polyethylene, polypropene, styrene, polyester and nylon. Before 2004, due to the low production capacity of benzene downstream products in China, the products can basically meet the demand and some products are exported. However, the production capacity of the benzene downstream products in China has increased rapidly in the past two years, and especially with the large-scale construction of the production apparatuses of styrene, phenol, aniline, cyclohexanone and the like, the demand in the benzene market is increased greatly. Therefore, China turns into a pure importing country from an exporting country of benzene. It is expected that in the next few years, Chinese benzene will not meet the downstream market demand. For China, it is of great significance to develop a new technology for synthesis of aromatic hydrocarbons from resources other than petroleum, particularly under the current energy supply situation of "rich coal reserve, but deficiency in oil and natural gas". The technology of synthesis of aromatics through methanol and dimethyl ether or through synthesis gas directly opens up a new technology route for BTX production from coal. It can effectively relieve the contradiction between scant supply of the aromatic hydrocarbons in China and excess capacity of methanol, and has a good prospect.

The technology of synthesizing aromatic hydrocarbons by catalytic reaction of methanol or dimethyl ether has been explored, and it has been demonstrated up to pilot plant tests. However, this technology needs multiple reaction steps. Firstly, the synthesis gas is converted into methanol or dimethyl ether, etc. Then methanol or dimethyl ether is converted to aromatics via the so-called MTA process. In this process, the $H_2/CO$ ratio in the synthesis gas shall be 2 for methanol synthesis. If the synthesis gas comes from coal gasification and the $H_2/CO$ proportion is generally 0.5-1, then the $H_2/CO$ proportion must be adjusted to 2 by the water-gas shift process, which is a high energy consumption and high water consumption process. In addition, the technology is susceptible to fluctuations in the methanol market. It was reported that the aromatic hydrocarbons can be possibly synthesized via direct conversion of the synthesis gas using the Fe/MnO-ZnZSM-5, which converted the synthesis gas into the light olefin intermediates via Fischer-Tropsch reaction and then to aromatics on the zeolite. It showed a higher zinc content benefited the formation of the aromatic hydrocarbons products and reducing the formation of the gas phase low carbon hydrocarbons. However, the selectivity of the aromatics in that process was low, which was only about 53% (Chinese Journal of Catalysis, 2002, 23, Vol. 4, 333-335). Fe—Pd/HZSM-5 was also studied for synthesis of the aromatics. Under the temperature of 340° C., pressure of 8.62 MPa and space velocity of 3000 $h^{-1}$, CO conversion reached 75.7%, but the selectivity of the aromatics in liquid phase products was only 32.0% (Energy Fuels, 2014, 28, 2027-2034). Pd/$SiO_2$+HZSM-5 or H-mordenite catalyst was also used to synthesize the aromatics through the route from methanol. The influence of different reaction conditions on the product distributions and yield were discussed. The aromatics selectivity was also low, only about 50%, and the products are mainly tetramethylbenzene and pentamethylene (Journal of Catalysis, 1984, 87, 136-143). Therefore, it is particularly urgent to develop a technology for synthesis of aromatics from synthesis gas with a high selectivity in order to alleviate the scant supply of the aromatics in China.

SUMMARY OF THE INVENTION

In view of the above problems, the present invention provides a catalyst and a method for synthesis of aromatic hydrocarbons through direct conversion of synthesis gas.

The present invention is described as follows:

A catalyst is a composite catalyst constituting of components A+B and is formed by compounding the Catalyst Component A and Catalyst Component B in a mechanical mixing mode. The active ingredient of catalyst A is active metal oxides; and catalyst B is one or both of ZSM-5 zeolite and metal modified ZSM-5. The active metal oxide is one or more than two of MnO, $MnCr_2O_4$, $MnAl_2O_4$, $MnZrO_4$, ZnO, $ZnCr_2O_4$ and $ZnAl_2O_4$; and preferably, the active metal oxide is one or more than two of MnO, $MnCr_2O_4$, $MnAl_2O_4$ and $MnZrO_4$.

A spacing between the geometric centers of the active metal oxide particles of the Catalyst Component A and that of the particles of the Catalyst Component B is 5 nm-4 mm, preferably 5 nm-1 mm and more preferably 5 nm-500 μm.

A mass ratio of the active ingredients in the Catalyst Component A and the Catalyst Component B is within a range of 0.1-20 times, and preferably 0.3-5.

The Catalyst Component A includes a dispersing agent; the dispersing agent is one or two of $Al_2O_3$, $Cr_2O_3$, $ZrO_2$ and $TiO_2$; the active metal oxide is dispersed in the dispersing agent; and the content of the dispersing agent in the Catalyst Component A is 0.05-90 wt %, and the rest is the active metal oxide.

The active metal oxides are composed of oxide grains with a size of 5-30 nm, and a large quantity of oxygen vacancies exist on the surface of the metal oxides, at a distance of 0.3 nm from the surfaces of the grains toward the internal direction of the grains, wherein the molar amount of the oxygen atoms is less than 80% of the theoretical stoichiometry of the oxygen atoms in the oxides; preferably, the oxygen atoms is 80%-10% of the theoretical stoichiometry of the oxides, more preferably 60-10% and most preferably 50-10%; the contents of the surface oxygen vacancies are defined as: 100% minus the percentage of the surface oxygen atoms among the stoichiometric amount of oxygen in theory; and thus the corresponding oxygen vacancy concentration is preferably 20-90%, more preferably 40-90% and most preferably 50-90%.

The preparation procedure of the preferable active metal oxide is as follows: immersing the metal oxide in the solution of etching agents by adopting one or more of such etching agents as oleic acid, hexamethylenetetramine, ethylenediamine, ammonia, hydrazine hydrate, etc.; heating the above suspension at 100-150° C., and preferably 120-140° C. for 30-90 minutes; then taking out the suspended matter for washing and filtering to obtain active metal oxide material having a large amount of surface oxygen vacancies; and then drying and reducing the filtered matter in an atmosphere which is inert gas or a gas mixture of inert gas and a reducing atmosphere, wherein the gas in the inert atmosphere is one or more of $N_2$, He and Ar; the reducing atmosphere is one or more of $H_2$ and CO; a volume ratio of the inert gas to the reducing gas in the gas mixture is 100/10-0/100; the processing time is 0.5-5 hours; and processing temperature is 20-500° C., and preferably 200-400° C.

The molar ratio of silica to alumina ($SiO_2/Al_2O_3$) of ZSM-5 is 20-1000, preferably 150-800, and more preferably 300-800.

The ZSM-5 zeolite macroscopically presents one or more of hexagonal prism sheets or ellipsoidal particles or pie-shaped particles, which can be observed by a scanning electron microscope. ZSM-5 is formed by accumulated ZSM-5 grains.

The ZSM-5 zeolite has a multilevel hierarchical pore structure which comprises macropores, mesopores and micropores; the macroporous specific surface area and the mesoporous specific surface area occupy 5-25% of the total specific surface area, and preferably 5-15%; the microporous specific surface area occupies 40-90%, and preferably 40-70%. The micropores are pore channels with a diameter less than 2 nm; the mesopores are pore channels with a diameter of 2 nm-50 nm; the macropores are pore channels with a diameter larger than 50 nm;

ZSM-5 crystals have microporous structures which exhibit typical MFI structures with ordered channels; the micropores of the ZSM-5 zeolite are located in the ZSM-5 crystals; and the mesopores and the macropores are disordered, formed by the stacked crystals.

The sheet structure is a hexagonal prism sheet; (010) surface presents a hexagon; six sides are equal or not equal; the axis perpendicular to the (100) surface of the MFI structure is the 'a' axis; the axis perpendicular to (010) surface is the 'b' axis, its length or thickness corresponding to the distance between the upper and lower hexagonal end surfaces; the axis which is simultaneously perpendicular to the 'a' axis and the 'b' axis is the 'c' axis; the thickness of the 'b' axis is 30-500 nm; the length of the 'a' axis is 500-1500 nm; the length of the 'c' axis is 500-2000 nm; and preferably, the thickness of the 'b' axis is 30-200 nm.

The ZSM-5 crystals with the ellipsoidal shape has a long axis and two short axes, with a size of 500 nm-10 μm, 500 nm-5 μm and 500 nm-5 μm, respectively.

The pie-shaped ZSM-5 zeolite exhibits a shape similar to the shape of the chessman of Chinese chess or Chinese drum; the upper end surface and the lower end surface are planes; the two end surfaces and the cross section are circular or ellipsoidal surfaces; the side wall surface presents an arc shape which is protruded outwards or not outwards, i.e., the area of the cross section is greater than or equal to the area of their two end surfaces; the length or thickness of the 'b' axis is the distance of the upper end surface and the lower end surface, in a range of 30-500 nm; the length of the 'a' axis is 100-800 nm; the length of the 'c' axis 500-800 nm; and preferably, the thickness of the 'b' axis is 30-200 nm.

Metal modified ZSM-5 is the ZSM-5 modified by one or two of Zn, Ga, Sn, Mn, Ag and Zr; and the total content of the modifying metals is 0.5-2 wt. %.

The mechanical mixing adopts one or more of the following methods: mechanical agitation, ball milling, rocking bed mixing and mechanical grinding.

A method for synthesis of aromatic hydrocarbons through direct conversion of synthesis gas uses synthesis gas as the feeding, which is operated in a fixed bed or a moving bed reactor. The adopted catalyst is the catalysts described above.

The pressure of the synthesis gas is 0.1-6 MPa; the reaction temperature is 300-600° C., and preferably, the reaction temperature is 400-600° C.; and the space velocity is 500-8000 $h^{-1}$.

The volume ratio of $H_2/CO$ in the synthesis gas for reaction is 0.2-3.5, and preferably 0.3-2.

The bifunctional composite catalyst is used for synthesis of aromatic hydrocarbons through one-step direct conversion of synthesis gas. The selectivity of aromatic hydrocarbons in all hydrocarbon products is 50-85%, and preferably 64-85% while the selectivity of the methane byproduct is less than 15%, preferably less than 10%, and more preferably less than 5%.

The present invention has the following advantages:

1. It is different from the traditional technology for synthesis of aromatic hydrocarbons through methanol (MTA for short), this invention provides a technology for synthesis of aromatic hydrocarbons through one-step direct conversion of synthesis gas.

2. The composite catalysts in the patent are simple and easy to prepare and require mild preparation conditions. The reaction process has an extremely high product yield and selectivity, with the selectivity of aromatics reaching 50-85%, and preferably 64-85% while the selectivity of a methane side product very low (<15%), preferably <10%, and more preferably <5%. The present invention has strong potentials for industrial applications.

3. The ZSM-5 zeolite in the patent has a shape of sheet or ellipse or pie with the nano structure; and the spacing between catalyst A and catalyst B is favorable for timely diffusion and conversion of the reaction intermediates, avoiding the side reactions and secondary reactions and consequently enhancing the selectivity of aromatic hydrocarbons.

DESCRIPTION OF PREFERRED EMBODIMENTS

The present invention is further illustrated below by embodiments, but the scope of claims of the present invention is not limited by the embodiments. Meanwhile, the embodiments only give some conditions for achieving the purpose, but it doesn't mean that the conditions must be satisfied to achieve the purpose.

Embodiment 1

I. Preparation of the Catalyst a Component
(I) Synthesizing ZnO Material with Polar Surface Through an Etching Method:

(1) weighing 0.446 g (1.5 mmol) of $Zn(NO_3)_2 \cdot 6H_2O$; weighing 0.480 g (12 mmol) of NaOH; weighing 30 ml of deionized water and adding to the container; stirring for a duration greater than 0.5 h to uniformly mix a solution; increasing the temperature to 160° C. with the reaction time of 20 h; decomposing precipitate into zinc oxide; naturally cooling to room temperature; centrifugally separating the reaction liquid to collect the centrifugally separated precipitate; and washing with deionized water twice to obtain ZnO oxide;

(2) ultrasonically mixing an etching agent with ZnO oxide uniformly under ambient temperature; immersing the ZnO oxide in the solution of the etching agent; and generating a complexing or direct reduction reaction by the etching agent and the zinc oxide; heating the above suspension; then taking out for washing and filtering, to obtain active nano ZnO material having a large amount of surface oxygen vacancies.

In Table 1: the mass ratio of the catalyst to the etching agent is 1:3. The mass ratio of the oleic acid to the hexamethylenetetramine is 1:1, without solvent. The mass ratio of the oleic acid to the hydrazine hydrate is 95:5, without solvent. Specific treatment conditions include temperature, treatment time and atmosphere types as shown in Table 1 below.

(3) Drying or drying and reducing:

after centrifuging or filtering the above obtained products and washing the products with deionized water, drying or drying and reducing the products in an atmosphere which is inert gas or a gas mixture of inert gas and a reducing atmosphere, wherein the inert gas is one or more of $N_2$ and CO, a volume ratio of the inert gas to the reducing gas in the gas mixture is 100/10-0/100, the temperature of drying and reducing is 350° C., and time is 4 h. ZnO material with abundant oxygen vacancies on the surface is obtained. The samples and their preparation conditions thereof are shown in Table 1 below. The oxygen vacancies on the surface are defined as: 100% minus the percentage of the surface oxygen atoms to the stoichiometric amount of oxygen in the oxides in theory.

TABLE 1

Preparation of ZnO Material, the Preparation Conditions and the Structural Features

| Sample Number | Etching Agent | Temperature/° C. and Carrier Gas (V/V) | Time/Minute | Drying or Drying and Reducing Temperature/° C. and Atmosphere | Surface Oxygen Vacancy |
|---|---|---|---|---|---|
| ZnO 1 | oleic acid-hexamethylenetetramine | 100, $N_2$ | 30 | 30, $N_2$ | 21% |
| ZnO 2 | oleic acid | 100, 5% $H_2/N_2$ | 30 | 300, 5% $H_2/N_2$ | 45% |
| ZnO 3 | oleic acid | 120, 5% CO/Ar | 60 | 350, 5% CO/Ar | 67% |
| ZnO 4 | oleic acid-5 wt % hydrazine hydrate | 140, 5% $H_2$/Ar | 60 | 310, 5% $H_2$/Ar | 73% |
| ZnO 5 | ethylenediamine | 100, 5% $NH_3$/Ar | 30 | 250, 5% $NH_3$/Ar | 30% |
| ZnO 6 | ethylenediamine | 140, 5% NO/Ar | 90 | 150, 5% NO/Ar | 52% |
| ZnO 7 | 20 wt % ammonium hydroxide | 100, Ar | 30 | 120, 5% CO/Ar | 22% |
| ZnO 8 | 20 wt % ammonium hydroxide | 140, 5% $NH_3$/5% NO/Ar | 90 | 400, He | 29% |

The surface oxygen vacancies are the oxygen vacancies on the catalyst surface within a distance range of 0.3 nm from the very surfaces of the grains to the internal direction of the grains. The surface oxygen vacancies are defined as: 100% minus the percentage of the surface oxygen atoms to the stoichiometric amount of oxygen in the oxides in theory.

As a reference example, ZnO 9 is prepared, which is not etched in step (2) and has no oxygen vacancy on the surface; and metal Zn 10 is a Zn sample, which is completely reduced.

(II) Synthesizing MnO material with a polar surface by an etching method: the preparation process is the same as that of the above ZnO. The difference is that, the precursor of Zn is changed for the corresponding precursor of Mn, which is one of manganous nitrate, manganese chloride and manganese acetate (manganous nitrate herein).

The etching process is the same as step (2) in above (I), and the process of drying or drying and reducing is the same as the preparation processes of products ZnO 3, ZnO 5 and ZnO 8 in step (3) in above (I). The catalyst having a great number of surface oxygen vacancies is synthesized. The surface oxygen vacancies are 67%, 29% and 27%.

Corresponding products are defined as MnO 1-3.

(III) Synthesizing nano $ZnCr_2O_4$, $ZnAl_2O_4$, $MnCr_2O_4$, $MnAl_2O_4$ and $MnZrO_4$ spinel with high surface area and high surface energy:

selecting corresponding nitrate, zinc nitrate, aluminum nitrate, chromic nitrate and manganous nitrate as precursors according to the chemical composition of the spinel, and mixing the precursors with urea at room temperature in water; aging the above mixed liquid; then taking out the mixed liquid for washing, filtering and drying; and calcining the obtained solid under an air atmosphere to obtain spinel oxide which grows along the (110) crystal plane direction. The sample is also treated by the etching method to synthesize the catalyst with a great number of surface oxygen vacancies. The etching process and post-treatment process are the same as step (2) and step (3) in above (I). The sample has a large surface area and many surface defects, and can be applied to catalyzing the conversion of synthesis gas.

The samples and preparation conditions thereof are listed in Table 2 below. Similarly, the surface oxygen vacancies are defined as: 100% minus the percentage of the surface oxygen atoms to the stoichiometric amount of oxygen in the oxides in theory.

nitrate, zinc sulfate and other Zn precursors as raw materials and precipitate the metal components using one or more of natrium hydroxide, ammonium bicarbonate, ammonium carbonate and sodium bicarbonate which are mixed at room temperature. Herein, taking zinc nitrate and natrium hydroxide as an example, the molar concentration of $Zn^{2+}$ in the reaction liquid is 0.067M; the ratio of molar fractions of $Zn^{2+}$ and precipitant may be 1:8; and then aging is conducted at 160° C. for 24 hours to obtain carrier $Cr_2O_3$, $Al_2O_3$ or $ZrO_2$ dispersed ZnO oxide, and the contents of the dispersing agents in catalyst A are 0.1 wt %, 10 wt % and 90 wt %.

The etching process is the same as the preparation processes of products ZnO 3, ZnO 5 and ZnO 8 in step (2) in above (I). The catalysts having a great number of surface oxygen vacancies are prepared. The surface oxygen vacancies are 65%, 30% and 25%, respectively. The post-treatment process is the same as the step (3) in above (I).

The corresponding products from top to bottom are denoted as Dispersed oxides 1-3.

The same method is used to obtain the $Cr_2O_3$, $Al_2O_3$ or $ZrO_2$ dispersed MnO oxides, wherein the contents of the dispersing agents in the Catalyst A are 5 wt %, 30 wt % and 60 wt %. The surface oxygen vacancies are 62%, 27% and 28%, respectively. Corresponding products from top to bottom are denoted as Dispersed oxides 4-6.

II. Preparation of the Catalyst B Component (ZSM-5):

(I) Sheet-Like ZSM-5 Zeolite

Preparing sheet-like ZSM-5 zeolite according to the following molar ratio of substances:

Si source is selected from one or more of TEOS, silica sol and white carbon black; and the aluminum source is selected from one or more of sodium metaaluminate, $Al(OH)_3$, AlOOH and aluminium isopropoxide.

TABLE 2

Preparation of Spinel Material and their Structural Features

| Sample Number | Stoichiometric Ratio of Metal Elements in Spinel and Final Molar Concentration of Metal in Water (mmol/L) | Aging Temperature/° C. and duration h | Calcination Temperature ° C. and duration h | Etching Agent, Temperature/° C. Atmosphere and duration/min | Surface Oxygen Vacancy |
|---|---|---|---|---|---|
| Spinel 1 | ZnCr = 1:2, Zn is 50 mM | 120, 24 | 600, 48 | oleic acid, 120, 5% $H_2$/Ar, 60 | 41% |
| Spinel 2 | ZnAl = 1:2, Zn is 50 mM | 130, 20 | 700, 24 | oleic acid, 120, 5% $H_2$/Ar, 60 | 72% |
| Spinel 3 | MnCr = 1:2, Mn is 50 mM | 140, 18 | 750, 16 | oleic acid, 120, 5% $H_2$/Ar, 60 | 83% |
| Spinel 4 | MnAl = 1:2, Mn is 50 mM | 145, 16 | 800, 10 | oleic acid, 120, 5% $H_2$/Ar, 60 | 20% |
| Spinel 5 | MnZr = 1:2, Mn is 50 mM | 150, 12 | 900, 3 | oleic acid, 120, 5% $H_2$/Ar, 60 | 24% |
| Spinel 6 | MnAl = 1:2, Mn is 50 mM | 140, 18 | 750, 16 | oleic acid, 120, 5% $H_2$/Ar, 60 | 73% |
| Spinel 7 | MnZr = 1:2, Mn is 50 mM | 140, 20 | 750, 16 | oleic acid, 120, 5% $H_2$/Ar, 60 | 68% |

(IV) $Cr_2O_3$, $Al_2O_3$ or $ZrO_2$ dispersed active metal oxides $Cr_2O_3$, $Al_2O_3$ or $ZrO_2$ are used as the carrier or dispersing agent for the active metal oxides. Such dispersed active metal oxides are prepared through a precipitate deposition method by taking $Cr_2O_3$, $Al_2O_3$ or $ZrO_2$ as carriers. Taking the preparation of dispersed ZnO as an example, commercial $Cr_2O_3$, $Al_2O_3$ or $ZrO_2$ carrier is dispersed in a solution in advance, and then taking one or more of zinc acetate, zinc Because urea is firstly absorbed to the 'b' axis, the growth of crystals in the direction of the 'b' axis is inhibited. The crystals firstly grow along the 'a' axis and the 'c' axis, thus forming ZSM-5 in the format of sheets.

The preparation procedure is: dissolving the aluminum source in water; successively adding a silicon source, a template agent (tetrapropylammonium hydroxide TPAOH) and urea; stirring to obtain a homogeneous solution and then placing it into a hydrothermal reactor to allow a hydrothermal reaction; subsequently washing the obtained product with water; and finally calcining under an air atmosphere for 6 hours to remove the template agent, and thus the ZSM-5 in sheets are obtained, wherein the thickness of the ZSM-5 sheets is 10-200 nm and mesopores and macropores co-exist in the ZSM-5.

The samples, their preparation conditions and the structural features thereof are listed in Table 3 below.

Without the template agent in the process of nucleation and growth, the crystals grow into the thermodynamically most stable spheroidal structure. Because of the influence of gravity and mass transfer during crystallization under static conditions, the growth rates of the crystals in the directions of the 'a' axis, the 'b' axis and the 'c' axis are inconsistent. Therefore, the ellipsoidal shaped ZSM-5 is formed.

TABLE 3

Preparation of sheet-like ZSM-5 and their Structural Features

| Sample Number | Si Source | Aluminum Source | Molar Ratio | Hydrothermal Temperature (° C.), Duration (Day) | Hexagonal Prism Sheet, Lengths of the 'a' Axis, 'b' Axis and 'c' Axis (nm) | Percentage of Mesoporous and Macroporous Specific Surface Area in Total Specific Surface Area |
|---|---|---|---|---|---|---|
| Sheet 1 | TEOS | sodium metaaluminate | $SiO_2$: 0.005 $Al_2O_3$: 0.02 TPAOH: 10 $H_2O$: 0.1 urea | 160, 6 | 500, 200, 800 | 12 |
| Sheet 2 | silica sol | $Al(OH)_3$ | $SiO_2$: 0.0033 $Al_2O_3$: 1 TPAOH: 30 $H_2O$: 1 urea | 200, 2 | 800, 200, 1200 | 14 |
| Sheet 3 | TEOS | AlOOH | $SiO_2$: 0.05 $Al_2O_3$: 1 TPAOH: 30 $H_2O$: 3 urea | 180, 3 | 1500, 500, 1500 | 25 |
| Sheet 4 | silica sol | aluminium isopropoxide | $SiO_2$: 0.00125 $Al_2O_3$: 2 TPAOH: 50 $H_2O$: 5 urea | 180, 4 | 900, 80, 1000 | 15 |

The preparation procedure of the sheet-like ZSM-5 modified by metal Zn, Ga, Sn, Mn, Ag and Zr is: the preparation procedure is the same as the procedure of product Sheet 1 in the above (I); the difference is: after completing the preparation of ZSM-5 and calcining out the template agent, one of $Zn(NO_3)_2$, $Ga(NO_3)_3$, $Sn(NO_3)_2$, $Mn(NO_3)_2$, $AgNO_3$ and $Zr(NO_3)_2$ with a desired amount is dissolved in deionized water, which is brought onto ZSM-5 by incipient impregnation, for 3 hours; and after drying at 110° C., ZSM-5 is calcined under the air atmosphere at 600° C. for 6 hours. The total contents of the modifying metal are 0.5 wt. %, 1 wt. %, 0.5 wt. %, 2 wt. %, 1 wt. % and 2 wt. %, respectively. The resulting zeolites have the same dimension and the same silica/alumina ratio as those of the sample Sheet 1.

The corresponding products are defined as Sheet 5-10.

(II) Ellipsoidal Shape ZSM-5

The procedure is described as follows:

Firstly, two solutions A and B are prepared, wherein the Solution A contains the following components: NaOH+ silica sol+$H_2O$ which are uniformly mixed by stirring;

The Solution B contains the following components: $NaAlO_2$+$H_2O$ which are uniformly mixed and stirred;

next, the Solution B is dropwise added to Solution A; the dripping rate is two drops per minute; the solution B is dripped and simultaneously stirred uniformly; then the Solution B is moved into the hydrothermal reactor to conduct the hydrothermal reaction, subjected to crystallization under static conditions without the template agent, and finally calcined under the air atmosphere at 600° C. for 6 hours, and thus ellipsoidal ZSM-5 are obtained. Mesopores and macropores co-exist in the ellipsoidal ZSM-5.

The samples and preparation conditions thereof are shown in Table 4 below.

TABLE 4

Preparation of Ellipsoidal ZSM-5 and their Structural Features

| Sample Number | A Liquid | B Liquid | Dropwise addition Temperature (° C.) | Hydrothermal Temperature (° C.), Time (Day) | Sizes of the Long Axis and Two Short Axes | Percentage of Mesoporous and Macroporous Specific Surface Area in Total Specific Surface Area |
|---|---|---|---|---|---|---|
| Ellipsoid 1 | 0.4 g NaOH + 18 g silica sol + 19 g $H_2O$ | 0.015 g $NaAlO_2$ + 13 g $H_2O$ | 25 | 160, 6 | 10 μm, 200 nm, 5 μm | 13 |

TABLE 4-continued

Preparation of Ellipsoidal ZSM-5 and their Structural Features

| Sample Number | A Liquid | B Liquid | Dropwise addition Temperature (° C.) | Hydrothermal Temperature (° C.), Time (Day) | Sizes of the Long Axis and Two Short Axes | Percentage of Mesoporous and Macroporous Specific Surface Area in Total Specific Surface Area |
|---|---|---|---|---|---|---|
| Ellipsoid 2 | 0.8 g NaOH + 28 g silica sol + 28 g $H_2O$ | 0.24 gNaAlO$_2$ + 28 g$H_2O$ | 35 | 200, 2 | 5 μm, 1 μm, 1 μm | 17 |
| Ellipsoid 3 | 1.2 g NaOH + 35 g silica sol + 35 g $H_2O$ | 0.075 gNaAlO$_2$ + 44 g$H_2O$ | 15 | 180, 4 | 1 μm, 500 nm, 700 nm | 19 |

The preparation procedure of the Ellipsoidal ZSM-5 modified by metal Zn, Ga, Sn, Mn, Ag and Zr is: the preparation procedure is the same as the procedure of the product Ellipsoid 1 in the above (II); the difference is: after completing the preparation of ZSM-5 without the template agent and burning out the template agent, one of $Zn(NO_3)_2$, $Ga(NO_3)_3$, $Sn(NO_3)_2$, $Mn(NO_3)_2$, $AgNO_3$ and $Zr(NO_3)_2$ is dissolved in the deionized water according to a desired amount, which is brought onto ZSM-5 by incipient impregnation for 4 hours; and after drying at 110° C., ZSM-5 is calcined in air at 630° C. for 4 hours. The contents of the modifying metal are 0.5 wt. %, 1 wt. %, 0.5 wt. %, 2 wt. %, 1 wt. % and 2 wt. %, respectively. The obtained zeolites have the same dimension and the same silica/alumina ratio as those of the Ellipsoid 1.

The obtained products are denoted as Ellipsoid 4-9.

(III) Pie-Shaped ZSM-5

Preparing Pie-shaped ZSM-5 according to the following procedure:

Crystallization is allowed under static conditions with TPAOH as a template to obtain pie-shaped ZSM-5 crystals. At the early stage of crystal growth, crystals in the shape of nano sheets are formed. Because of a large ratio of $H_2O$/$SiO_2$ and relatively low concentration of the template agent around the crystals, the crystals have a sufficient space for continuously growing into a pie shape.

The procedure is: adding TPAOH to the silicon source, and then adding a certain amount of $H_2O$ to obtain the Solution A; stirring the Solution A in a water bath at 80° C. for 24 h; dissolving the aluminum source in NaOH solution to prepare the Solution B; adding the Solution B to the Solution A dropwise; then stirring for 3 hours; subsequently moving the resulting solution to a stainless steel reactor allowing crystallizing for 2 days; and after washing with water, calcining in air at 560° C. for 5 hours to burn out the template agent.

The samples and preparation conditions thereof are shown in Table 5 below.

TABLE 5

Preparation of Pie-Shaped ZSM-5 and the Structural Features

| Sample Number | Si Source | Aluminum Source | Molar Ratio | Hydrothermal Temperature (° C.), Duration (Day) | Lengths of the 'a' Axis, 'b' Axis and 'c' Axis (nm) | Percentage of Mesoporous and Macroporous Specific Surface Area in Total Specific Surface Area |
|---|---|---|---|---|---|---|
| Pie 1 | TEOS | sodium metaaluminate | $SiO_2$: 0.001 $Al_2O_3$: 0.5 TPAOH: 20 $H_2O$ | 160, 3 | 200, 150, 100 | 14 |
| Pie 2 | silica sol | Al(OH)$_3$ | $SiO_2$: 0.05 $Al_2O_3$: 0.5 TPAOH: 100$H_2O$ | 200, 1 | 500, 35, 500 | 16 |
| Pie 3 | TEOS | AlOOH | $SiO_2$: 0.002 $Al_2O_3$: 0.02-2 TPAOH: 200 $H_2O$ | 180, 2 | 800, 500, 800 | 20 |

Si source is selected from one or both of TEOS and silica sol; and the aluminum source is selected from one or more of sodium metaaluminate, Al(OH)$_3$, and AlOOH.

The preparation procedure of the pie-shaped ZSM-5 modified by metal Zn, Ga, Sn, Mn, Ag and Zr is: the preparation procedure is the same as the procedure for the Pie 1 in the above (III); the difference is: after completing the preparation of the Pie-shaped ZSM-5 and burning out the template agent, one of $Zn(NO_3)_2$, $Ga(NO_3)_3$, $Sn(NO_3)_2$, $Mn(NO_3)_2$, $AgNO_3$ and $Zr(NO_3)_2$ with a desired amount is dissolved in deionized water, which is brought onto ZSM-5 by incipient impregnation for 4 hours; and after drying at 110° C., ZSM-5 is calcined in air at 500° C. for 4 hours. The contents of the modifying metals are 0.5 wt. %, 1 wt. %, 0.5 wt. %, 2 wt. %, 1 wt. % and 2 wt. %, respectively. The resulting zeolites have the same dimension and the same silica/alumina ratio as those of the Pie 1.

The obtained samples are denoted as Pie 4-9.

III. Catalyst Preparation

The Catalyst Component A and the Catalyst Component B in the required ratio are added to the container and subjected to fast moving treatment of the material and/or the container so as to generate one or more of extrusion force, impact force, shear force and friction force, and to exert separation, crushing, uniform mixing and the like on the materials inside the container; by changing the temperatures and treatment atmospheres, the mechanical energy, thermal energy and chemical energy can be interconverted, thereby further enhancing the interaction between different components.

In the mechanical mixing process, the mixing temperature can be set as 20-100° C., and the mechanical mixing process can be conducted in a specific atmosphere or directly in the air. The atmosphere is one or more of: a) nitrogen and/or inert gas; b) mixed gas of hydrogen, nitrogen and/or inert gas, with the volume ratio of hydrogen in the mixed gas being 5-50%; c) mixed gas of carbon monoxide, nitrogen and/or inert gas, with the volume ratio of carbon monoxide in the mixed gas being 5-20%; and d) mixed gas of oxygen, nitrogen and/or inert gas, with the volume ratio of oxygen in the mixed gas being 5-20%. The inert gas is one or more of helium, argon and neon.

Mechanical stirring: mixing the Catalyst Component A and the Catalyst Component B with a stirring rod in a stirring tank; and regulating the mixing degree and the relative distance of the Catalyst Component A and the Catalyst Component B by controlling the stirring time (5 min-120 min) and the stirring rate (30-300 r/min).

Ball milling: Rolling at a high speed in a grinding tank by using abrasive materials and the catalysts; and producing strong impact force and milling on the catalysts to achieve the effects of dispersing and mixing the Catalyst Component A and the Catalyst Component B. The ratio of the abrasive materials (which can be stainless steel, agate and quartz; and the size range is 5 mm-15 mm) to the catalysts (the mass ratio scope is 20-100:1) is controlled to regulate the particle size and the relative distance of the catalysts.

Shaking table mixing: premixing the Catalyst Component A and the Catalyst Component B and placing the catalysts into the container; realizing the mixing of the Catalyst Component A and the Catalyst Component B by controlling the reciprocating oscillation or circumferential oscillation of a shaking table; and realizing uniform mixing and regulating the relative distance by regulating the oscillation speed (range: 1-70 r/min) and time (range: 5 min-120 min).

Mechanical grinding: premixing the Catalyst Component A and the Catalyst Component B and placing the catalysts into the container; and under certain pressure (range: 5 kg-20 kg), making relative motion and mixing (speed range: 30-300 r/min) by the grinding to achieve the effects of regulating the particle size and the relative distance of the catalyst components and realizing uniform mixing.

The samples, preparation conditions and the structural features are shown in Table 6 below.

TABLE 6

Preparation of Catalysts and their Structural Features

| | | | | Compounding Mode and Condition | | | | |
|---|---|---|---|---|---|---|---|---|
| Catalyst Number | Catalyst Component A | Catalyst Component B | Weight Ratio of A to B | mechanical agitation rate (r/min) and Time (min) | Grinding material, ball size, and the mass ratio of grinding material to catalyst | rocking bed oscillation speed (r/min) and time (min) | mechanical polishing pressure (kg) and relative movement rate (r/min) | Geometrical Center Distance of A and B Particles |
| A | ZnO 1 | Sheet 1 | 0.33 | 5, 30 | | | | 3 mm |
| B | ZnO 2 | Ellipsoid 1 | 0.5 | 100, 250 | | | | 500 μm |
| C | ZnO 3 | Sheet 1 | 2 | | 5 mm stainless steel ball, 50:1 | | | 52 μm |
| D | ZnO 4 | Ellipsoid 1 | 1 | | 6 mm stainless steel ball, 60:1 | | | 80 μm |
| E | ZnO 6 | Pie 1 | 1 | | | 5, 10 | | 2 mm |
| F | ZnO 8 | Ellipsoid 2 | 3 | | | 60, 100 | | 600 μm |
| G | ZnO 5 | Sheet 2 | 3 | | | | 5, 30 | 300 μm |
| H | Spinel 1 | Sheet 3 | 1 | 100, 300 | | | | 400 μm |
| I | Spinel 2 | Sheet 4 | 5 | | 6 mm agate ball, 100:1 | | | 30 μm |
| J | Spinel 3 | Sheet 5 | 1 | | | 70, 100 | | 500 μm |
| K | Spinel 4 | Ellipsoidal 2 | 3 | | | | 15, 200 | 150 μm |

TABLE 6-continued

Preparation of Catalysts and their Structural Features

| Catalyst Number | Catalyst Component A | Catalyst Component B | Weight Ratio of A to B | mechanical agitation rate (r/min) and Time (min) | Grinding material, ball size, and the mass ratio of grinding material to catalyst | rocking bed oscillation speed (r/min) and time (min) | mechanical polishing pressure (kg) and relative movement rate (r/min) | Geometrical Center Distance of A and B Particles |
|---|---|---|---|---|---|---|---|---|
| L | Spinel 5 | Pie 2 | 0.33 | | | | 20, 300 | 100 μm |
| M | MnO 1 | Sheet 7 | 1 | 100, 300 | | | | 400 μm |
| N | MnO 2 | Ellipsoid 3 | 3 | | 6 mm quartz, 100:1 | | | 15 μm |
| O | MnO 3 | Pie 4 | 2 | | 6 mm quartz, 100:1 | | | 15 μm |
| P | Dispersed oxide 2 | Sheet 3 | 1 | | | | 10, 100 | 100 μm |
| Q | Dispersed oxide 1 | Sheet 1 | 1 | 100, 250 | | | | 2 mm |
| R | Dispersed oxide 4 | Ellipsoid 1 | 3 | | 5 mm stainless steel ball, 50:1 | | | 50 μm |
| S | Dispersed oxide 3 | Pie 2 | 1 | | | | 10, 100 | 100 μm |
| T | Dispersed oxide 5 | Sheet 2 | 4 | | | 50, 60 | | 1 mm |
| U | Dispersed oxide 6 | Pie 3 | 3 | | | | 10, 100 | 100 μm |
| V | ZnO 1 | Ellipsoid 5 | 20 | | 5 mm stainless steel ball, 100:1 | | | 15 nm |
| W | MnO 1 | Pie 8 | 16 | 100, 200 | | | | 400 μm |
| X | ZnO 7 | Sheet 5 | 0.1 | | | | 20, 100 | 500 μm |
| P1 | MnO 1 | Sheet 6 | 1 | | | | 20, 300 | 100 μm |
| P2 | Spinel 1 | Sheet 8 | 1.5 | 60, 100 | | | | 2 mm |
| P3 | ZnO 1 | Sheet 9 | 4 | | 5 mm stainless steel ball, 50:1 | | | 15 nm |
| P4 | ZnO 3 | Sheet 10 | 4.5 | | | 50, 120 | | 500 μm |
| T1 | MnO 1 | Ellipsoid 4 | 2.5 | | | | 10, 200 | 200 μm |
| T2 | Spinel 1 | Ellipsoid 6 | 3 | | | | 20, 200 | 150 μm |
| T3 | ZnO 1 | Ellipsoid 7 | 5 | 100, 100 | | | | 1 mm |
| T4 | Spinel 3 | Ellipsoid 8 | 6 | | 10 mm stainless steel ball, 50:1 | | | 10 nm |
| T5 | Spinel 5 | Ellipsoida9 | 1.2 | | | 50, 100 | | 500 μm |
| Q1 | MnO 1 | Pie 3 | 4.8 | 10, 50 | | | | 500 μm |
| Q2 | Spinel 1 | Pie 5 | 10 | | | | 5, 100 | 200 μm |
| Q3 | ZnO 1 | Pie 6 | 12 | | | 70, 120 | | 500 μm |
| Q4 | Spinel 3 | Pie 7 | 8 | 120, 100 | | | | 1 mm |
| Q5 | ZnO 3 | Pie 9 | 15 | | 10 mm agate ball, 100:1 | | | 10 nm |
| S1 | Spinel 6 | Sheet 1 | 3 | | | | 10, 200 | 200 μm |
| S2 | Spinel 6 | Ellipsoid 4 | 1 | | 5 mm stainless steel ball, 50:1 | | | 50 μm |
| S3 | Dispersed oxide 4 | Ellipsoid 1 | 1.5 | | | 70, 120 | | 500 μm |
| S4 | ZnO 4 | Sheet 1 | 2 | | | | 20, 200 | 150 μm |
| S5 | Spinel 2 | sheet 1 | 2 | | | 70, 300 | | 400 μm |

TABLE 6-continued

Preparation of Catalysts and their Structural Features

| Catalyst Number | Catalyst Component A | Catalyst Component B | Weight Ratio of A to B | Compounding Mode and Condition | | | | Geometrical Center Distance of A and B Particles |
|---|---|---|---|---|---|---|---|---|
| | | | | mechanical agitation rate (r/min) and Time (min) | Grinding material, ball size, and the mass ratio of grinding material to catalyst | rocking bed oscillation speed (r/min) and time (min) | mechanical polishing pressure (kg) and relative movement rate (r/min) | |
| S6 | Spinel 7 | Sheet 1 | 1.5 | | 6 mm agate ball, 100:1 | | | 30 μm |
| S7 | Spinel 7 | Ellipsoid 4 | 2 | | | | 10, 300 | 100 μm |
| Comparison A | ZnO 9 | Sheet 1 | 3 | | | 20, 30 | | 2 mm |
| Comparison B | Zn 10 | Pie 1 | 2 | 60, 100 | | | | 2 mm |

Examples of Catalytic Reactions

A fixed bed reaction is taken as an example, but the catalysts are also applicable to a moving bed reactors. The apparatus is equipped with mass flow controllers and online product analysis chromatography (the tail gas of the reactor is directly connected with the metering valve of chromatography, and thus periodic and real-time sampling and analysis will be achieved).

2 g of the above catalyst in the present invention is placed in a fixed bed reactor. The air in the reactor is replaced with Ar; and then the temperature is raised to 300° C. in the $H_2$ atmosphere, and then the synthesis gas ($H_2$/CO molar ratio=0.2-3.5) is fed in. The pressure of the synthesis gas is 0.1-6 MPa. The temperature is raised to reaction temperature of 300-600° C., and the space velocity of the feed gas is controlled in a range of 500-8000 ml/g/h. The on-line chromatography is used to monitor and analyze the products.

The catalytic performance can be changed by changing the reaction temperature, pressure, space velocity and $H_2$/CO molar ratio in the synthesis gas. The selectivity of aromatic hydrocarbons (including benzene, toluene, xylene, trimethyl benzene and other aromatics) in all hydrocarbons is as high as 50%-85%, and the conversion of CO is 10%-60%. Because the hydrogenation activity of the metal oxides is not high, mass production of methane is avoided. The selectivity of the methane is low, and the total selectivity of methane, $C_{2-4}$ hydrocarbon, and $C_{5+}$ hydrocarbon (not including aromatics) is 15%-50%.

Table 7 lists the applications of some catalysts and their catalytic performance data.

TABLE 7

Applications of some invented catalysts and their catalytic performance data

| Embodiment | Catalyst | GHSV ($h^{-1}$) | Temperature (° C.) | $H_2$/CO Molar Ratio | Pressure (MPa) | CO Conversion % | Aromatics Selectivity % | $CH_4$ Selectivity % | $C_2$-$C_4$ Hydrocarbon Selectivity % | $C_{5+}$ Selectivity % |
|---|---|---|---|---|---|---|---|---|---|---|
| 1 | A | 2500 | 400 | 2 | 3.5 | 32.5 | 51.8 | 14.2 | 29.7 | 56.1 |
| 2 | B | 3000 | 400 | 3 | 3 | 42.3 | 55.5 | 5.3 | 31.2 | 63.5 |
| 3 | C | 3000 | 360 | 2 | 2.5 | 32.5 | 51.2 | 4.2 | 25.5 | 70.3 |
| 4 | D | 8000 | 350 | 1 | 2.5 | 18.6 | 50.6 | 5.1 | 39.8 | 55.1 |
| 5 | E | 1000 | 450 | 3.5 | 6 | 32.8 | 53.4 | 9.5 | 32.2 | 58.3 |
| 6 | F | 2000 | 300 | 0.5 | 6 | 33.3 | 54.8 | 6.6 | 33.1 | 60.3 |
| 7 | G | 3000 | 380 | 2.5 | 2.5 | 20.3 | 61.2 | 7.7 | 23.7 | 68.6 |
| 8 | H | 500 | 350 | 2.5 | 5 | 59.6 | 53.4 | 12.8 | 26.9 | 60.3 |
| 9 | I | 2300 | 350 | 1 | 3.5 | 23.3 | 80.5 | 4.2 | 12.2 | 83.6 |
| 10 | J | 2000 | 350 | 2.5 | 5 | 43.3 | 74.7 | 5.5 | 15.6 | 78.9 |
| 11 | K | 1000 | 400 | 2.5 | 3 | 25.7 | 53.2 | 9.1 | 30.6 | 60.3 |
| 12 | L | 2500 | 300 | 1 | 4 | 21.2 | 58.2 | 4.5 | 21.8 | 73.7 |
| 13 | M | 3000 | 400 | 0.5 | 4 | 15.5 | 81.5 | 6.2 | 8.7 | 85.1 |
| 14 | N | 3100 | 300 | 1 | 6 | 10.2 | 50.5 | 2.1 | 43.4 | 54.5 |
| 15 | O | 3200 | 300 | 1 | 5 | 13.3 | 50.9 | 3.2 | 30.5 | 66.3 |
| 16 | P | 3000 | 350 | 2.5 | 5 | 33.8 | 59.6 | 6.9 | 23.7 | 69.4 |
| 17 | Q | 3000 | 350 | 1 | 3 | 28.8 | 54.2 | 8.6 | 31.1 | 60.3 |
| 18 | R | 2100 | 500 | 1 | 4 | 28.6 | 80.5 | 4.4 | 9.4 | 86.2 |
| 19 | S | 2500 | 400 | 1 | 3 | 29.6 | 59.8 | 5.7 | 28.6 | 65.7 |
| 20 | T | 4000 | 400 | 2 | 4 | 20.3 | 51.1 | 9.4 | 31.6 | 59 |
| 21 | U | 3500 | 400 | 3 | 3 | 16.4 | 54.8 | 7.2 | 29.4 | 63.4 |
| 22 | V | 3000 | 450 | 2.5 | 4 | 21.2 | 58.4 | 8.3 | 26.9 | 64.8 |
| 23 | W | 2000 | 400 | 3 | 3 | 30.2 | 50.3 | 10.4 | 31.7 | 57.9 |
| 24 | X | 2500 | 400 | 0.3 | 4 | 16.8 | 62.1 | 5.3 | 24.6 | 70.1 |
| 25 | P1 | 3000 | 350 | 3 | 4 | 15.6 | 80.1 | 5.3 | 10.5 | 84.2 |
| 26 | P2 | 4500 | 400 | 2.5 | 3 | 11.8 | 61.3 | 8.2 | 19.6 | 72.2 |

TABLE 7-continued

Applications of some invented catalysts and their catalytic performance data

| Embodiment | Catalyst | GHSV (h$^{-1}$) | Temperature (° C.) | H$_2$/CO Molar Ratio | Pressure (MPa) | CO Conversion % | Aromatics Selectivity % | CH$_4$ Selectivity % | C$_2$-C$_4$ Hydrocarbon Selectivity % | C$_{5+}$ Selectivity % |
|---|---|---|---|---|---|---|---|---|---|---|
| 27 | P3 | 4000 | 400 | 3 | 4 | 28.5 | 55.8 | 4 | 35.7 | 60.3 |
| 28 | P4 | 2000 | 320 | 2.5 | 3 | 10.9 | 51.3 | 8.7 | 32.6 | 58.7 |
| 29 | T1 | 4000 | 450 | 3 | 4 | 20.1 | 64.1 | 3.2 | 26.3 | 70.5 |
| 30 | T2 | 4200 | 400 | 2.5 | 4 | 25.8 | 55.3 | 10 | 31.3 | 58.7 |
| 31 | T3 | 2500 | 350 | 3 | 3.5 | 18.3 | 51.2 | 5.3 | 21.6 | 73.1 |
| 32 | T4 | 3500 | 400 | 2.5 | 3 | 39 | 63.2 | 6.9 | 25 | 68.1 |
| 33 | T5 | 5000 | 400 | 3 | 3.5 | 50.7 | 51.3 | 8 | 33.8 | 58.2 |
| 34 | Q1 | 4000 | 350 | 2.5 | 4 | 29.2 | 56.1 | 7.8 | 26.9 | 65.3 |
| 35 | Q2 | 4200 | 400 | 2.5 | 2.5 | 22.4 | 52.5 | 4.1 | 33.9 | 62 |
| 36 | Q3 | 3500 | 350 | 3 | 4 | 38.3 | 57.1 | 6.3 | 26.9 | 66.8 |
| 37 | Q4 | 4000 | 350 | 2.5 | 4 | 19 | 52.3 | 4.5 | 35.1 | 60.4 |
| 38 | Q5 | 3000 | 400 | 3 | 3.5 | 34.2 | 61 | 6.7 | 30.4 | 62.9 |
| 39 | S1 | 1000 | 450 | 2 | 4 | 26.9 | 86.2 | 3.8 | 9.2 | 87 |
| 40 | S2 | 2000 | 500 | 3 | 3 | 30.2 | 82.1 | 5.1 | 7.5 | 87.4 |
| 41 | S3 | 1500 | 450 | 1 | 2 | 31.8 | 84.8 | 4.6 | 5.7 | 89.7 |
| 42 | S4 | 2500 | 450 | 2 | 3 | 45.2 | 54.7 | 15.3 | 23.3 | 61.4 |
| 43 | S5 | 1000 | 500 | 2 | 3 | 52.5 | 51.1 | 18.9 | 20.3 | 60.8 |
| 44 | S6 | 2000 | 500 | 2 | 4 | 35.6 | 84.3 | 4.6 | 7.2 | 88.2 |
| 45 | S7 | 1500 | 450 | 1 | 3 | 32.7 | 80.5 | 4.3 | 9.8 | 85.9 |
| Reference Example 1 | | 3000 | 400 | 2.5 | 3 | 40.1 | 21 | 31 | 39.8 | 29.2 |
| Reference Example 2 | | 2000 | 350 | 1 | 4 | 1.9 | 19.2 | 6.8 | 53.1 | 40.1 |
| Reference Example 3 | | 4000 | 450 | 3 | 3 | 30.5 | 6.8 | 12.6 | 74.5 | 12.9 |
| Reference Example 4 | | 2000 | 350 | 2.5 | 3 | 12.3 | 15.5 | 35.1 | 45.5 | 19.4 |
| Reference Example 5 | | 3000 | 400 | 1 | 4 | 44.6 | 10.2 | 19.1 | 62.3 | 18.6 |
| Reference Example 6 | | 3000 | 400 | 2 | 3.5 | 31.2 | 15.5 | 19.8 | 57.5 | 22.7 |
| Reference Example 7 | | 3000 | 450 | 2.5 | 4 | 28.6 | 13.6 | 7.9 | 63.3 | 28.8 |
| Reference Example 8 | Comparison A | 3200 | 320 | 3 | 2 | 3.6 | 30.7 | 19.1 | 44.5 | 36.4 |
| Reference Example 9 | Comparison B | 4000 | 400 | 3 | 4 | 39.8 | 7.6 | 51.2 | 33.2 | 15.6 |

The catalyst adopted in reference example 1 is metal ZnCo+Ellipsoid 1 of the Catalyst Component A. The molar ratio of Zn/Co=1/1. The mass ratio of ZnCo/ZSM-5=1/1. Other parameters and the mixing process are the same as those of the Catalyst C.

The catalyst adopted in reference example 2 is TiO$_2$ without surface oxygen vacancy in coupling with the Sheet 2 sample. Other parameters and the mixing process are the same as those of the Catalyst C.

The zeolite in the catalyst adopted in reference example 3 is a commercially available microporous ZSM-5 purchased from Nankai University Catalyst Company, wherein the silica alumina ratio is 30, which is coupled with ZnO 2.

The catalyst adopted in reference example 4 is featured with a distance of 5 mm between the metal oxide and the zeolite components. All other parameters and the mixing process are the same as those of the Catalyst C.

The catalyst adopted in reference example 5 is featured with the metal oxides component being located in the porous channels of the zeolite and is in close contact with the porous channels. All other parameters and the like are the same as those of the Catalyst C.

The catalyst adopted in reference example 6 is featured with the zeolite component having the ellipsoidal shape, but particle size of 10-20 μm. All other parameters and the mixing process are the same as those of the Catalyst C.

The catalyst adopted in reference example 7 is featured with the zeolite component having a shape of sheet, but a particle size of 5 μm and a thickness of the '13' axis of 700 nm. All other parameters and the mixing process are the same as those of the Catalyst C.

The catalyst adopted in reference example 8 is featured with the Catalyst Component A of ZnO 9, and the component B of sheet 1.

In reference example 9, the component A is Zn 10, and component B is Pie 1.

From the above table, there is a set of parameters of the composite catalysts are important, including the preferable ratio of the Catalyst Component A to the Catalyst Component B of 0.3-5, the preferable quantity of oxygen vacancies of 40-90, the preferable silica/alumina ratio of the zeolite of 150-800 and more preferable ratio of 300-800, the preferred thickness of the 'b' axis of 30-200 nm and the preferred distance of 5 nm-1 mm between the component A and the component B. Only when these preferred parameters are fulfilled simultaneously, a high CO conversion and a high selectivity of the aromatic hydrocarbons can be realized.

More description is illustrated as follows:

For the catalysts I, J, R and P1 in Table 7, the quantity of the oxygen vacancies of the Catalyst Component A is high, the 'b' axis of the zeolite of the Catalyst Component B is short, the silica/alumina ratio is high, and the distance between A and B, and the mass ratio of A/B are appropriate, and the above factors are within the preferred ranges. Therefore, the selectivity for the aromatic hydrocarbons is high, larger than 65%.

In contrast, for the Catalyst Q in Table 7, the quantity of the surface oxygen vacancies of the catalyst component A is high, the Catalyst B component is the zeolite of Sheet 1, and the silica/alumina ratio, the thickness of the 'b' axis and the mass ratio of A/B are all within the preferred ranges, but the distance between the component A and the component B is too far, which is 2 mm, not within the preferred range. Therefore, the selectivity of the desired aromatic hydrocarbons is low, which is 54.2%.

Moreover, the comparison between the embodiments S1-S7 shows that when all the above parameters fall in the preferred ranges defined in claims, the catalysts containing Mn oxides exhibits a higher activity than those Zn oxide-based catalysts at high temperatures. High temperature refers to a temperature between 400° C. and 600° C.

It can be seen that the catalysts defined in claim 1 of the present patent can be used for synthesis of aromatics through one-step direct conversion of synthesis gas, and the selectivity of aromatics can reach 50-85%, while the selectivity of the byproduct methane is very low and less than 15%. When specific structural parameters the catalysts and reaction conditions fall in the preferred ranges, selectivity of 60% for aromatics, and even 65% or higher selectivity can be realized, even under high temperature conditions.

We claim:

1. A composite catalyst comprising Catalyst A and Catalyst B, wherein the Catalyst A and Catalyst B are compounded by mechanical mixing, the Catalyst A comprises particles of a first metal oxide selected from the group consisting of MnO, $MnCr_2O_4$, $MnAl_2O_4$, $MnZrO_4$, ZnO, $ZnCr_2O_4$, $ZnAl_2O_4$ and combinations thereof; the Catalyst Component B comprises particles of at least one of ZSM-5 zeolite and metal modified ZSM-5, a spacing between geometric centers of the first metal oxide particles of the Catalyst A and geometric centers of the particles of at least one of ZSM-5 zeolite and metal modified ZSM-5 in the Catalyst Component B particles is 5 nm-4 mm.

2. The composite catalyst according to claim 1, wherein the spacing is 5 nm-1 mm.

3. The composite catalyst according to claim 1, wherein a mass ratio of the first metal oxide in the Catalyst A and the Catalyst B is within a range of 0.1-20.

4. The composite catalyst according to claim 1, wherein the Catalyst A comprises a dispersing agent; the dispersing agent is a second metal oxide selected from the group consisting of $Al_2O_3$, $Cr_2O_3$, $ZrO_2$, $TiO_2$, and combinations thereof; the first metal oxide is dispersed in the dispersing agent; and the content of the dispersing agent in the Catalyst A is 0.05-90 wt. %, and the rest is the first metal oxide.

5. The composite catalyst according to claim 1, wherein the first metal oxide is composed of oxide grains with a size of 5-30 nm, and oxygen vacancies exist on the surface of the first metal oxide, at a distance of 0.3 nm from the surfaces of the grains toward the internal direction of the grains, wherein the molar amount of oxygen atoms is less than 80% of the theoretical stoichiometry of the oxygen atoms in the first metal oxide.

6. The composite catalyst according to claim 1, wherein molar ratio of silica to alumina ($SiO_2/Al_2O_3$) of ZSM-5 is 20-1000;
the ZSM-5 zeolite is formed by agglomerated ZSM-5 grains.

7. The composite catalyst according to claim 1, wherein the metal modified ZSM-5 is the ZSM-5 modified by one or two of Zn, Ga, Sn, Mn, Ag and Zr; and the total content of the modifying metals is 0.5-2 wt. %.

8. A method for synthesis of aromatic hydrocarbons through direct conversion of synthesis gas comprising feeding a synthesis gas into a fixed bed or a moving bed reactor loaded with the composite catalyst of claim 1 to effect the direct conversion.

9. The method according to claim 8, wherein the direct conversion is conducted under the following conditions: pressure of the synthesis gas: 0.1-6 MPa; reaction temperature: 300-600° C.; and space velocity: 500-8000 $h^{-1}$.

10. The method according to claim 8, wherein the synthesis gas comprises $H_2$/CO in a volume ratio of 0.2-3.5.

11. A composite catalyst comprising Catalyst A and Catalyst B, wherein the Catalyst A and Catalyst B are compounded by mechanical mixing; the Catalyst A comprises particles of a first metal oxide selected from the group consisting of MnO, $MnCr_2O_4$, $MnAl_2O_4$, $MnZrO_4$, ZnO, $ZnCr_2O_4$, $ZnAl_2O_4$ and combinations thereof; the Catalyst Component B comprises particles of at least one of ZSM-5 zeolite and metal modified ZSM-5; the Catalyst A comprises a dispersing agent; the dispersing agent is a second metal oxide selected from the group consisting of $Al_2O_3$, $Cr_2O_3$, $ZrO_2$, $TiO_2$, and combinations thereof; the first metal oxide is dispersed in the dispersing agent; and the content of the dispersing agent in the Catalyst A is 0.05-90 wt. %, and the rest is the first metal oxide.

12. A composite catalyst comprising Catalyst A and Catalyst B, wherein the Catalyst A and Catalyst B are compounded by mechanical mixing; the Catalyst A comprises particles of a first metal oxide selected from the group consisting of MnO, $MnCr_2O_4$, $MnAl_2O_4$, $MnZrO_4$, ZnO, $ZnCr_2O_4$, $ZnAl_2O_4$ and combinations thereof; the Catalyst Component B comprises particles of at least one of ZSM-5 zeolite and metal modified ZSM-5; the first metal oxide is composed of oxide grains with a size of 5-30 nm, and oxygen vacancies exist on the surface of the first metal oxide, at a distance of 0.3 nm from the surfaces of the grains toward the internal direction of the grains; and the molar amount of oxygen atoms is less than 80% of the theoretical stoichiometry of the oxygen atoms in the first metal oxide.

* * * * *